United States Patent
Bowden et al.

[19]

[11] Patent Number: 5,935,102
[45] Date of Patent: Aug. 10, 1999

[54] STEERABLE ELECTRODE CATHETER

[75] Inventors: Russell W Bowden, Tyngsboro, Mass.; Gary S. Falwell, Manchester, N.H.; Charles A. Gibson, Malden, Mass.; Richard B. Stevens, Chelmsford, Mass.; Debbie E. Stevens-Wright, Lowell, Mass.

[73] Assignee: C. R. Bard, Murray Hill, N.J.

[21] Appl. No.: 08/736,321

[22] Filed: Oct. 23, 1996

Related U.S. Application Data

[63] Continuation of application No. 08/518,521, Aug. 23, 1995, Pat. No. 5,611,777, which is a continuation-in-part of application No. 08/061,718, May 14, 1993, abandoned.

[51] Int. Cl.⁶ .................................................. A61M 37/00
[52] U.S. Cl. ............................ 604/95; 607/122; 600/585
[58] Field of Search ........................... 604/95, 264, 280; 128/642, 656, 657, 658, 772; 607/119, 122

[56] References Cited

U.S. PATENT DOCUMENTS

| | | | |
|---|---|---|---|
| 3,416,531 | 12/1968 | Edwards | 604/95 |
| 3,452,740 | 7/1969 | Muller | 604/95 |
| 3,470,876 | 10/1969 | Barchilon | 604/95 |
| 3,503,385 | 3/1970 | Stevens | 128/657 |
| 3,552,384 | 1/1971 | Pierie et al. | 604/95 |
| 3,729,008 | 4/1973 | Berkovits | 607/125 |
| 4,813,434 | 3/1989 | Buchbinder et al. | 604/95 |
| 4,860,769 | 8/1989 | Fogarty et al. | 607/119 |
| 4,920,980 | 5/1990 | Jackowski | 607/123 |
| 4,921,482 | 5/1990 | Hammerslag et al. | 604/95 |
| 4,960,134 | 10/1990 | Webster, Jr. | 607/116 |
| 4,960,411 | 10/1990 | Buchbinder | 604/95 |
| 4,976,688 | 12/1990 | Rosenblum | 604/95 |
| 4,998,916 | 3/1991 | Hammerslag et al. | 604/95 |
| 5,037,391 | 8/1991 | Hammerslag et al. | 604/95 |
| 5,125,896 | 6/1992 | Hojeibane | 604/95 |
| 5,176,126 | 1/1993 | Chikama | 604/95 |
| 5,195,968 | 3/1993 | Lundquist et al. | 604/95 |
| 5,254,088 | 10/1993 | Lundquist et al. | 604/95 |
| 5,327,906 | 7/1994 | Fideler . | |
| 5,395,329 | 3/1995 | Fleischhacker et al. . | |
| 5,397,321 | 3/1995 | Houser et al. . | |
| 5,423,771 | 6/1995 | Imran . | |
| 5,456,664 | 10/1995 | Heinzelman et al. . | |

FOREIGN PATENT DOCUMENTS

| | | |
|---|---|---|
| 0 605 796 | 7/1994 | European Pat. Off. . |
| 0 616 794 | 9/1994 | European Pat. Off. . |
| WO 94/11057 | 5/1994 | WIPO . |

*Primary Examiner*—Corrine M. McDermott
*Assistant Examiner*—Bhisma Mehta
*Attorney, Agent, or Firm*—Darby & Darby

[57] ABSTRACT

A steerable catheter includes control handle having a generally tubular housing with a longitudinal slot therein in which an axially or longitudinally movable two-part slideblock resides, and a generally cylindrical, rotatably mounted thumbwheel surrounding a distal portion of the tubular housing, for controlling the axial translation of the slideblock. The pullwire passes into the distal end of the control handle and is only secured to the proximal part of the two-part slideblock so as to prevent the user from placing the pullwire under compression. A tip radius adjusting wire is attached to and extends distally from a slide actuator in the control handle into and through the main catheter shaft portion. The free distal end of the tip radius adjusting wire is selectably locatable at different positions. The radius of curvature of the tip portion, when deflected, depends upon how far distally into the deflectable tip portion the radius adjusting wire has been advanced by the user. The electrode catheter thus has a deflectable tip whose radius of curvature is adjustable over a relatively wide range.

4 Claims, 2 Drawing Sheets

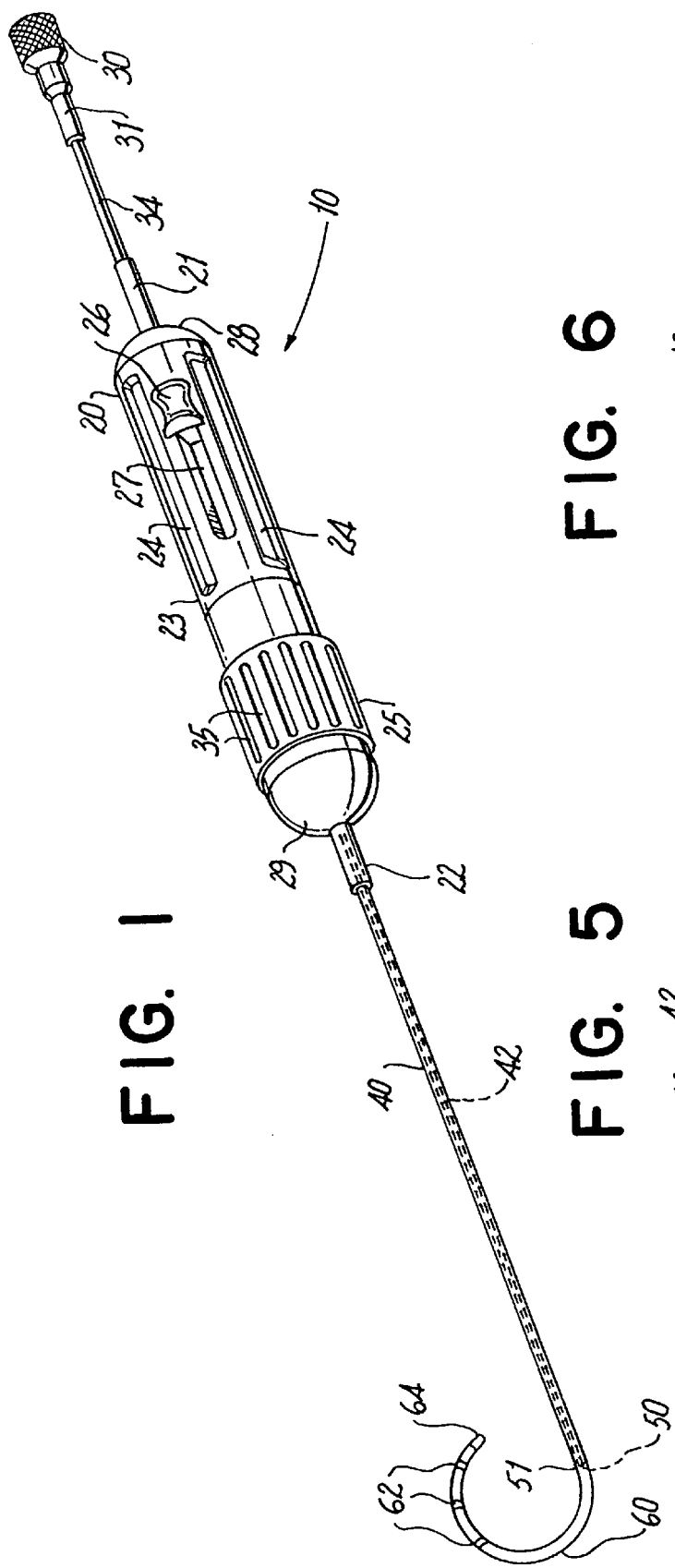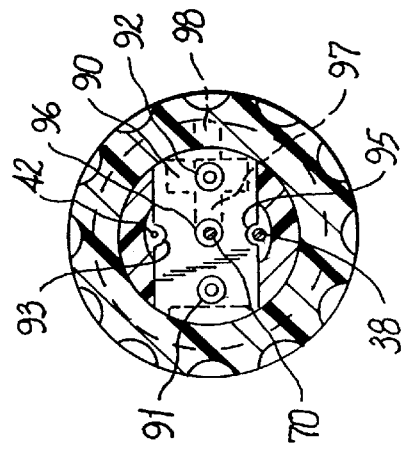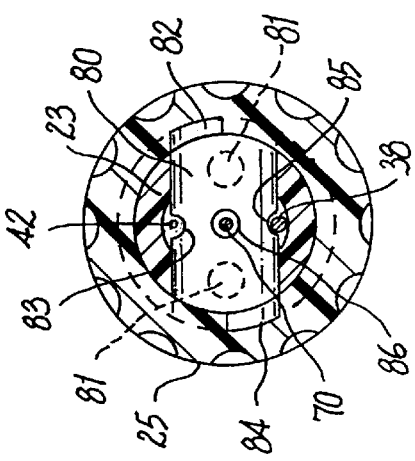

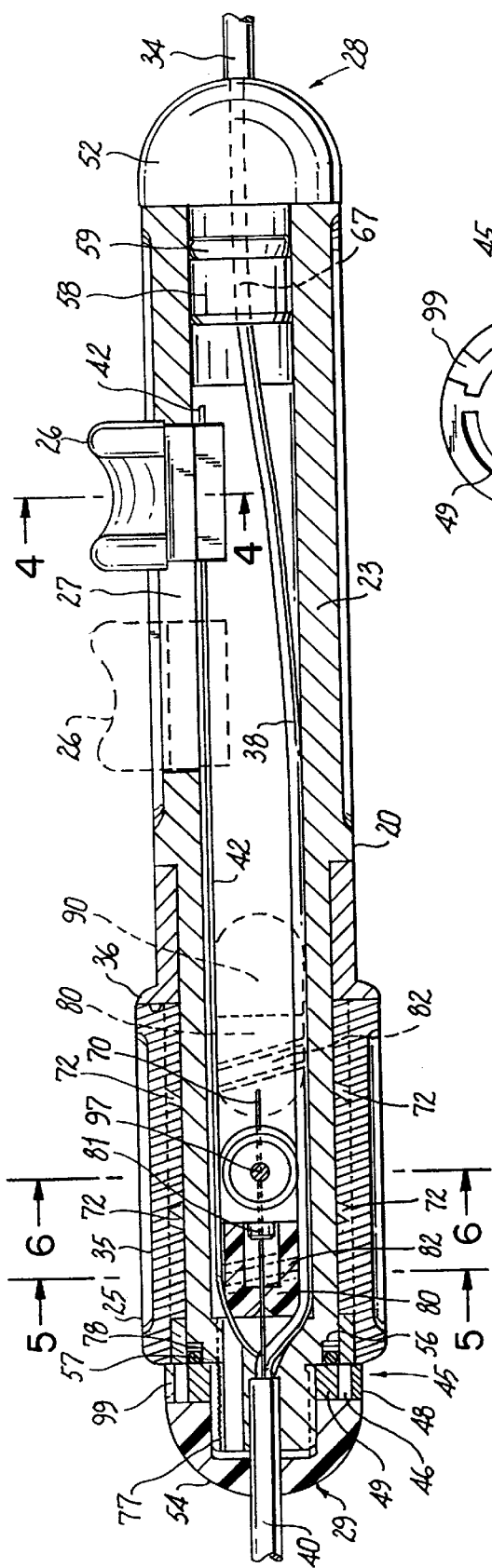
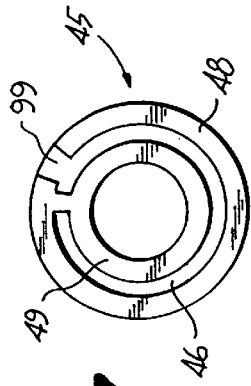
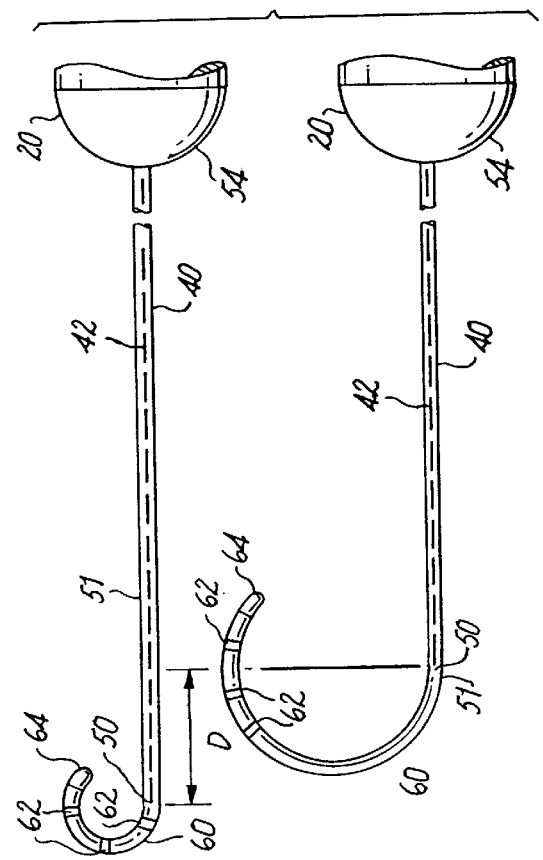
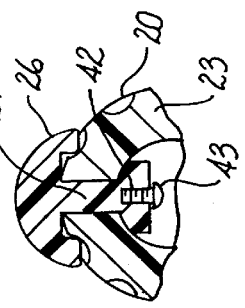

STEERABLE ELECTRODE CATHETER

This is a continuation of application Ser. No. 08/518,521, filed Aug. 23, 1995, now U.S. Pat. No. 5,611,777, which is a Continuation-in-Part Application of application Ser. No. 08/061,718 filed May 14, 1993, abandoned.

FIELD OF THE INVENTION

This invention relates to steerable catheters. More particularly, the invention relates to a manually controllable actuator handle of particular utility in controlling a deflectable electrode catheter tip of the type used for endocardial catheter recording, mapping, ablating and other surgical procedures.

BACKGROUND OF THE ART PERTAINING TO THE INVENTION

The clinical role of endocardial catheter recording and mapping is to direct ablation, surgical, and drug therapies in the treatment of supra-ventricular tachycardia, ventricular tachycardia, atrial flutter, atrial fibrillation and other arrhythmias. The success and advancement of current therapies is dependent upon the development and use of more precise localization techniques which will allow accurate anatomical determination of abnormal conductive pathways and other arrhythmogenic sites. Historically, the electrophysiologist has had to compromise between placing the catheter in the place of greatest clinical interest and areas which are anatomically accessible.

Open heart surgery to perform electrophysiological recording and mapping has largely been supplanted by cardiac catheterization performed under local anesthesia in the electrophysiology lab. Prior art catheter placement has been generally restricted to areas which can be repeatedly accessed by the electrophysiologist. These areas include the HRA (high right atrium), the RVA (right ventricular apex), the RVOT (right ventricular outflow tract), the coronary sinus and the HIS bundle. To obtain meaningful information about additional placement sites, the number of electrograms recorded over a given area may be increased, and the precise position of the electrode array of the distal tip portion of the catheter may be varied. Some of these additional sites include atrial sites above the tricuspid and mitral valves, ventricular sites circumferential to the mitral and tricuspid valve leaflets, distal areas of the coronary sinus and great cardiac vein, the AV nodal area and the left ventricle, to name a few.

One area of advancement in improving localization techniques and accessing additional recording sites includes the use of steerable catheters. One type of prior art steerable catheter offers improved maneuverability to specific, otherwise inaccessible sites by providing catheters shaped specifically to access a particular site. Although perhaps useful for some less inaccessible sites, the use of this type of catheter is limited, not very practical, and not helpful in reaching sites requiring active articulation during placement. Three such pre-shaped catheters are described in U.S. Pat. Nos. 3,503,385 issued to Stevens, 3,729,008 issued to Berkovits, and 4,860,769 issued to Forgerty, each of which is incorporated herein by reference.

Another type of prior art steerable catheter attempts to improve placement maneuverability by providing catheters having deflecting tips. These catheters include a relatively soft and flexible distal tip portion of a certain length attached to a proximal shaft made from a relatively stiffer material. Generally, the tip may be selectively deflected but only in a prescribed arc, i.e., the tip bends in one planar direction, with the bend having a fixed, predetermined radius of curvature. Some examples of deflecting tip catheters are described in U.S. Pat. Nos. 4,920,980 issued to Jackowski, 4,960,411 issued to Buchbinder, and 4,960,134 issued to Webster, each of which is also incorporated herein by reference. In devices of this type, a pullwire attached to the distal tip portion at or near the tip is pulled proximally while the catheter shaft is restrained, thus causing the tip to deflect. Alternatively, the pullwire is restrained while the shaft portion is advanced distally, producing the same effect. Various means are known for causing the tip to bend in a predetermined plane and direction.

A disadvantage of the above-described preformed and deflecting tip type catheters is that the tip of the catheter in each case may be deflected or steered only in a prescribed configuration which cannot be altered during its placement. That is, the steerable tip has a radius of curvature which is fixed, thus restricting the accessibility of the distal tip to certain anatomical sites without additional significant efforts of the electrophysiologist maneuvering the catheter exteriorly of the patient, and some sites may not be accessible at all. Such excessive maneuvering of the catheter exteriorly of the patient is difficult, frustrating, time consuming and inefficient to the physician performing a delicate procedure, and is thus inherently more risky for the patient undergoing that procedure. Most serious is the increased exposure of the patient, physicians and technicians to dangerous X-ray radiation which is used for fluoroscopic examination during procedures of this type.

Many of the desired sites require that the catheter traverse paths having many sharp bends and be able to negotiate multiple changes of direction through any or all of the three perpendicular planes of movement. Four-way steerable catheters have been developed in an attempt to provide a catheter with the above-described multi-planar maneuverability. As examples, such four-way steerable catheters are described in U.S. Pat. Nos. 3,470,876 issued to Barchilon, and 4,921,482, 4,998,916 and 5,037,391 issued to Hammerslag, each of which is also incorporated herein by reference. While such four-way steerable catheters may be improvements over two-way steerable catheters of this general type, the four-way steerable devices similarly suffer the disadvantage that the tips can deflect in only one predetermined configuration, that is, having a fixed, predetermined radius of curvature.

As a result of the above described disadvantage of prior art steerable catheters, the electrophysiologist must obtain and maintain not one but a set of similar steerable electrode catheters for use during any single clinical evaluation of a patient. For example, the user will have on hand a catheter having a steerable tip having a small radius of curvature; another with a medium radius of curvature and a third with a relatively large radius of curvature. While this availability of differently radiused tips is beneficial, it is often not known by the electrophysiologist which size will be required at any given moment during a diagnostic or therapeutic intracardiac procedure. Moreover, similar tip placements may require different radiused tips from one individual to another, even those of the same general body size and mass. When it is discovered by the electrophysiologist that a catheter then placed in a patient has an incorrectly radiused tip for the required procedure, the catheter must be completely withdrawn from the patient (through whichever one of the femoral, subclavian, jugular or brachial approaches was used), and a new properly radiused electrode catheter tip must be reintroduced into the heart. This substitution may take up to two hours or more to complete, including the time required to precisely reposition the electrode tip.

Moreover, the initially selected, but improperly sized catheter must generally be discarded, never having been actually used for its intended purpose, as such devices are intended as "single use only" devices, for a variety of safety reasons. Steerable catheters are relatively expensive devices, and this waste of an otherwise good device is especially troublesome.

Deflectable catheter tips of the type just described are generally resiliently biased to some degree to return to a straight configuration when not acted upon by the various prior art mechanisms for causing tip deflection. Another drawback with such catheters, as a result of this resiliency, is the sometimes undesired tendency of the tip to return to an undeflected position, or to merely change the amount of deflection, during the course of the electrophysiological procedure.

Furthermore, it is frequently necessary to rotate the entire catheter tip portion by applying torque to the catheter shaft by rotating the entire control handle. Some prior art catheters include steering control mechanisms or actuators which are located at a single particular radial location on the control handle. In use, however, when such handles are rotated, the electrophysiologist often loses a degree of control over the device, as the steering control mechanism is rotated to some position which is less easily manipulated.

OBJECTS OF THE INVENTION

The object of the invention is to provide an improved steerable electrode catheter which overcomes the foregoing problems and difficulties in the use of existing steerable electrode catheters.

Another object of the invention is to provide a control handle for a steerable catheter which maintains the deflectable catheter tip in its deflected position until the user changes the set amount of deflection.

A further object is to provide a steerable catheter tip having a variable radius of curvature, which radius of curvature can be varied during a procedure.

A still more specific object of the invention is to provide an improved control handle for use with a steerable catheter which is of a particular utility for endocardial catheter recording.

A still further specific object is to provide a control handle which can apply tension to a deflectable tip pullwire, but which is incapable of placing the pull cable under compression, and which is easy to use and relatively inexpensive to manufacture.

Yet still another object of the invention is to provide a steerable catheter control handle with which a tip deflection may be controlled regardless of the angular position of the handle about its longitudinal axis in the user's hand.

SUMMARY OF THE INVENTION

A steerable catheter includes a control handle, a main catheter shaft and a deflectable catheter distal tip portion. The catheter distal tip portion has an off-access lumen through which a pullwire extends, connecting the steering control mechanism of the control handle to a point near the distal end of the flexible tip portion. The proximal end of the main catheter shaft is secured to the distal end of the handle. The control handle includes a generally tubular housing having a longitudinal slot therein in which an axially or longitudinally movable two-part slideblock resides, and a generally cylindrical, rotatably mounted thumbwheel surrounding a distal portion of the tubular housing, for controlling the axial translation of the slideblock. The pullwire passes into the distal end of the control handle and is secured to the proximal part of the two-part slideblock.

Extending outwardly from each side of the longitudinal slot and integral with the lateral portions of the distal part of the slideblock is a single external helical thread or projection, i.e., one thread or helical "wing" on each lateral side of the distal part. The cylindrical thumbwheel is rotatably and coaxially mounted on the generally tubular housing, surrounding the longitudinal housing slot in which the slideblock is held. Internal helical threads on the cylindrical thumbwheel engage the external threads or projections protruding from the sides of the slideblock distal portion. Upon rotation of the thumbwheel by the user's thumb, or thumb in combination with one or more other fingers, the two-part slideblock is caused to travel proximally within the control handle housing, thus placing the pullwire in tension and pulling the pullwire proximally. Accordingly, the deflectable tip is caused to assume a deflected or bent configuration, due to the relatively softer material from which the tip portion is constructed, as compared to the main catheter shaft.

In order to prevent the user from placing the pullwire under compression, which compression can cause the pullwire to kink and ultimately fracture, the two parts of the slideblock are not joined together. Only the distal portion of the slideblock carries the external threads or projections. The pullwire passes through the distal part of the slideblock, however, and is secured only to the proximal part thereof. In this manner, the distal part of the slideblock can draw the pullwire proximally when the thumbwheel is rotated in the appropriate direction. But upon reversal of the thumbwheel, the distal part slides freely distally over the pullwire. Only the natural resiliency of the distal tip portion acts to return that tip portion to its undeflected condition.

A tip radius adjusting means comprises a relatively stiff shaft, spring, tube or similar member, as compared to the stiffness of the distal tip portion of the catheter. The shaft is preferably a wire or a wire within a spring which is attached to and extends distally from a slide actuator in the control handle into and through the main catheter shaft portion. The free distal end of the tip radius adjusting wire is selectably located at different positions, ranging from proximal to the boundary or junction between the main catheter shaft and the distal tip portion, to any more distal position within the relatively soft, deflectable tip portion, within the axial limit of its travel as controlled by the slide actuator. The radius of curvature of the tip portion, when deflected, depends upon how far distally into the deflectable tip portion the adjusting wire has been advanced by the user. In this way, the electrode catheter according to the invention has a deflectable tip whose radius of curvature is adjustable over a relatively wide range.

Once a radius of curvature has been selected by the electrophysiologist, deflection or steering of the catheter distal tip portion is thus accomplished without axial movement of any external control handle parts, allowing the catheter to be more easily held in its relative position with respect to the surgical site. The handle is also generally tubular and symmetrical about its longitudinal axis, thus allowing rotation about that axis by the electrophysiologist without affecting either the desired curvature of the catheter tip portion or the physician's access to the cylindrical thumbwheel. Mechanical advantage achieved by employing the above described screw thread arrangement allows for precise movement of the deflectable tip with minimum effort and reduces the possibility of accidental axial movement of the pullwire caused, for example, by resiliency of the tip portion. In this way, frictional resistance provides a passive locking mechanism of the tip deflection.

Other objects and features of the present invention will become apparent from the following detailed description of the preferred embodiment considered in conjunction with the accompanying drawings. It is to be understood, however, that the drawings are designed solely for the purposes of illustration and not as a definition of the limits of the invention.

BRIEF DESCRIPTION OF THE DRAWINGS

FIG. 1 is a perspective view of a deflectable tip steerable electrode catheter according to the invention;

FIG. 2 is a partial cross sectional view of the catheter of FIG. 1;

FIG. 3 is an illustration of how the distal advancement of the tip radius adjusting wire affects the radius of curvature of the tip bend;

FIG. 4 is a axial sectional view of the slide actuator taken along line 4—4 of FIG. 2;

FIGS. 5 and 6 are similarly axial sectional views taken along lines 5—5 and 6—6, respectively, of FIG. 2; and FIG. 7 is a plan view of the indicator ring of the control handle of FIG. 2.

DETAILED DESCRIPTION OF THE PREFERRED EMBODIMENT

FIG. 1 depicts a preferred embodiment of the steerable electrode catheter 10 of the present invention. The steerable electrode catheter comprises a control handle 20, an elongated flexible main catheter shaft 40, and a relatively soft steerable or deflectable tip portion 60. As described below, an electrophysiologist manipulates the tip portion 60 by means of the control handle and control wires which pass from the handle through the main shaft to the tip portion assembly. Generally speaking, the device may be described as an insulated electric conductor for use during electrophysiology studies for temporary intracardiac electrocardiographic recording, mapping, stimulation and/or therapy, including intracardiac ablation.

The tip portion 60 may be provided with a number of conductive ring electrodes 62 (three shown in FIG. 1)and a conductive tip or cap electrode 64, all of which are mechanically secured to the tip portion 60 at desired positions. The ring electrodes 62 and cap electrode 64 are preferably made of platinum. The ring electrodes 62 preferably range from two millimeters to four millimeters in length and are either 6 French or 7 French in size, depending upon the specific intended use of the catheter, although other sizes are also commonly employed. Spacing between the electrodes may range from one millimeter to one centimeter, again depending upon the particular type of electrode catheter. It will be readily understood by those skilled in the art that these details, including the many possible variations thereto, concerning the construction and location of the conductive electrodes 62,64 are entirely conventional and well known in the field of cardiac electrode catheters.

The proximal end of the catheter 10 is preferably provided with a cable connector 30 for electrical connection to a recording device (not shown) or some other device for capturing electrical signals sensed by the ring electrodes 62 and cap electrode 64. Such a recording device (not shown) may also include means or delivering electrical energy through the catheter conductive electrodes to cardiac tissue as desired, for pacing, diagnostic stimulation or therapeutic ablation or some other purpose, such as might be involved in medical research. The manner and details of construction of the connector 30 are not pertinent to the present invention, but it is preferred that the connector 30 have a knurled or textured surface for ease of gripping or manipulation by the physician, who will generally be wearing one (and possibly two) medical gloves on his or her hands. The connector 30 is secured to the handle 20 by a length of hollow, relatively flexible catheter shaft material 34 or other tubular stock. A strain relief 31 is preferably provided at the junction between the interconnecting shaft 34 and the connector 30, as is customary. It is also preferred that a similar strain relief 21 is provided at the junction of shaft 34 and the proximal end of the control handle 20, and another strain relief 22 is provided at the junction of the catheter main shaft 40 and the distal end of the control handle 20 to which the main shaft 40 is fixedly secured, such as by bonding.

As will be readily apparent, fine electrical conductors, such as wires (not shown), are electrically connected to each of the ring electrodes 62 and cap electrode 64. The ring electrodes 62 are preferably welded to their respective conductors, and the cap electrode 64 is preferably soldered to its conductive wire. These signal wires (not shown) pass through an internal bore or lumen in the tip portion 60, through an internal bore or lumen in the main shaft 40, into and through the control handle 20 as will be described in more detail below, and through the interconnecting shaft 34 for ultimate electrical connection, for example by crimping or soldering, to respective conductive contacts (not shown) of the connector 30. The signal wires are preferably individually electrically insulated and therefore may advantageously pass through and share a single lumen.

As further depicted in FIG. 1, the control handle 20, which will be described in detail below, generally comprises a tubular, substantially axially symmetric housing 23 has a distal end 29 and a proximal end 28 and a longitudinal axis therethrough, the housing axis being substantially coaxial with the proximal end of main shaft 40 and the distal end of interconnecting shaft 34. The tubular housing 23 nearer its proximal end 28 preferably has a plurality of longitudinal indentations or grooves 24 for ease of gripping the device. A cylindrical, coaxially rotatably mounted thumbwheel 25 is positioned on the housing 23 near its distal end 29, for manipulation of the steerable tip portion 60, by rotation of the thumbwheel 25 about its longitudinal axis, to be explained below. The thumbwheel 25 is advantageously provided with a plurality of evenly spaced, longitudinally oriented grooves 35 for improving the user's ability to rotate the thumbwheel 25. In use, when the control handle 20 is held in one's hand, the tubular housing 23 is held in the palm with four fingers wrapped—therearound, and the thumbwheel 25 is rotated by the user's thumb. Alternatively, the user may cradle or hold the housing 23 with just three fingers in order to more precisely rotate the thumbwheel 25 with both the thumb and index finger.

Also, generally, the control handle 20 is provided with a slide actuator 26 which travels proximally and distally in a longitudinal slot 27 in the tubular housing 23, located substantially proximally of the thumbwheel 25 and in the general area of the longitudinal grooves 24 in the housing 23 outer surface. The slide actuator 26 is attached to a relatively stiff shaft 42, preferably a relatively stiff wire or wire within a spring, which passes distally through the control handle and into the main catheter shaft 40. The shaft 42 may also comprise a hypotube within the catheter shaft 40 secured to a wire extending from the handle into the shaft 40. For ease of description, the radius adjustment member 42 will be referred to hereafter as a wire.

In the main catheter shaft 40, the wire 42 (shown in phantom lines in FIG. 1) has a free distal end 50. When the slide actuator 26 is in its most proximal position in the handle slot 27, the distal end 50 of the wire 42 extends to the junction 51 between the tip portion 60 and the stiffer, main catheter shaft 40. In this position, the tip portion 60 will be deflected (by rotation of thumbwheel 25) into a configuration having a relatively large radius of curvature. By advancing the slide actuator 26 distally, the user advances the wire 42 past the junction 51 into the softer distal tip portion 60. When the tip 60 is then deflected, the deflected tip configuration will have a relatively smaller radius of curvature, as explained below in more detail in connection with FIG. 3.

The overall length of the main shaft 40 and flexible tip portion combined preferably ranges from about 60 to 130 centimeters. The particular length selected for use in a given situation is purely a matter of physician preference, based upon medical judgment, training, the intended procedure to be performed and the anatomy of the individual patient.

Referring now to FIG. 2, the construction of control handle 20 is described in detail. Reference numerals identified in connection with FIG. 1 are consistently used to refer to the same components in FIG. 2 and in FIGS. 3–6. In FIG. 2, certain elements, such as strain reliefs 21,22 are not illustrated for the sake of clarity.

The proximal end 28 of the handle 20 comprises an end cap 52 having a reduced diameter plug section 58 fitted with a sealing O-ring 59. In manufacture, end cap 52 is adhesively bonded or sealed to tubular 10 housing 23 of the handle 20. A substantially axial bore 67 passes through the end cap 52 for accommodating passage of the electrically conductive signal wires connecting the ring and tip electrodes 62,64 to the electrical connector 30 of the device 10. A relatively flexible sheath 38 is secured to the distal end of the plug section 58 for guiding the fine electrically conductive wires from one end of the control handle to the other and into catheter main shaft 40, without exposing the delicate signal wires to potentially damaging mechanical movement of the internal parts of the control handle. Positioning of the sheath 38 within the central cavity of the tubular housing 23 is maintained by a lower longitudinal groove 95 formed in the proximal part 90 of a two-part slideblock and a corresponding lower longitudinal groove 85 in the distal part 80 of the slideblock, as seen more clearly in FIGS. 5 and 6, and as will be further described below.

Referring to FIGS. 2 and 4, slide actuator 26 is axially slidably supported in longitudinal groove 27 formed in the tubular housing 23 of the control handle 20. Radius of curvature adjustment wire 42 is secured, for example, by set screw 43, to the interior end of the slide actuator 26. In a similar manner to the positioning of wire sheath 38, wire 42 is also protected from accidental engagement with moving parts within the control handle 20 by resting in an upper longitudinal groove 93 of proximal part 90 of the slideblock and corresponding upper longitudinal groove 83 of the distal part 80 of the two-part slideblock, as seen more clearly in FIGS. 5 and 6. Adjustment wire 42 extends from the slide actuator 26 distally through the interior of the control handle tubular housing 23 and into the main catheter shaft 40, as described hereinabove.

At the distal end of the control handle 20, the generally cylindrical, fluted, axially rotatable thumbwheel 25 is supported on the housing 23 by circumferential shoulder 36 on the outer surface of the housing wall. The structure and operation of the thumbwheel 25 will be described in greater detail below.

Distal of the housing portion supporting the thumbwheel 25 is a reduced diameter sealing seat 56 in which one or more annular spacers 78 and a resilient rubber O-ring 57 are snugly held in place. The spacers 78 serve in the manufacturing and assembly process to finely adjust the initial or baseline torque required to rotate the thumbwheel 25.

A tip deflection indicator ring 45 is supported by the threaded distal end portion 77 of the tubular housing 23, and rests against the sealing O-ring 57 and the distal-most annular face of the cylindrical thumbwheel 25. The indicator ring 45 comprises an inner, annular ring 49 supported by and connected to an outer annular ring 48, the rings 49,48 being separated by an annular space 46. A distally protruding flat tab (not shown) is preferably provided on the distal-most annular face of the thumbwheel 25 and slidably mates into the annular groove 46. By virtue of the construction of the indicator ring 45, as illustrated in FIG. 7, the annular groove or slot 46 ensures that the thumbwheel 25 can travel only approximately one full revolution about the handle axis, due to the interference between the thumbwheel flat tab (not shown) and the connecting support structure attaching the inner annular ring 49 to the outer ring 48 of indicator ring 45. The outer annular ring 48 is further provided with a through hole 99 as seen in FIGS. 2 and 7 so that the protruding flat tab (not shown) may be visually observed when the thumbwheel 25 is rotated to a particular position. That position is selected to be the fully relaxed or undeflected position of the distal tip portion 60 of the electrode catheter 10. In this way, the user can be assured, for example, during retraction of the electrode catheter 10 through the vascular approach, that the distal tip is in its undeflected state. Without an indicator, such assurance is not always possible even under direct fluoroscopic inspection.

An internally threaded end cap 54 completes the overall assembly of the control handle 20. The end cap 54 fits over the catheter main shaft 40 which is adhesively bonded to the tubular housing 23. In actual manufacture, the threaded end cap 54 at the distal end 29 of the control handle 20 is also sealed and adhesively secured to the control handle tubular housing 23.

Now referring to FIG. 2 in conjunction with FIGS. 5 and 6, it is seen that a two-part slideblock comprises a distal part 80 and a proximal part 90. Both the distal part 80 and proximal part 90 are mounted in a longitudinal slot within the interior of control handle housing 23. The deflection tip pullwire 70 passes through the central through holes 86 and 96, respectively, of the distal part 80 and proximal part 90 of the slideblock. While the distal part 80 slides freely on pullwire 70, the proximal part 90 is releasably secured to the pullwire 70 by a rotatable pin 97 supported within a lateral bore through part 90, which can be rotated via a through hole 98 in the tubular housing 23 of the handle 20. As previously mentioned, both the distal part 80 and proximal part 90 of the slideblock include upper longitudinal grooves 83,93 and lower longitudinal grooves 85,95 for permitting passage of the radius of curvature adjusting wire 42 and the conductive wire protecting sheath 38 therearound, respectively, without causing any mechanical interference therewith. In this described embodiment, threaded nylon-tipped set screws 91,92 are mounted to the distal face of the proximal part 90 for engagement with the rotatable pin 97 to lock the pin 97, and thus the pullwire 70, in position in the slideblock.

As is seen in FIG. 2, the arrangement of the radius adjusting 42 within the housing 23 causes that wire 42 to navigate a relatively bent pathway at the distal end of the handle 20. An alternative, preferred embodiment for attachment of the wire 42 to the slide actuator 26 is now described.

In this alternative preferred embodiment, the slide actuator 26 extends slightly further radially inwardly toward the housing longitudinal axis, and the radial position of the actuator 26 is rotated 90 degrees away from the viewer with respect to the radial position shown in FIG. 2. Next, the left-most hole 81 in the distal part 80 of the slideblock is modified to be a through hole, and the nylon-tipped set screw 91 of the proximal part 90 of the slideblock is supplanted by a through hole. The rotating pin 97 is also cut down to two-thirds of its original length. Now the radius adjusting wire 42 can pass through the slideblock in a more direct, straighter path from the slide actuator 26 into the main catheter body 40, thus avoiding the abovementioned potential disadvantage.

The distal part 80 of the slideblock includes helically angled, laterally disposed external threads or wings 82,84. When mounted within the tubular housing 23 of the handle 20, the wings 82,84 engage and travel within the internal helical thread 72 of the cylindrical thumbwheel 25. Accordingly, upon rotation of the thumbwheel 25 in a first direction, the distal portion 80 of the slideblock is forced to travel proximally, thus pushing the proximal portion 90 of the slideblock in a proximal direction. This places tension on pullwire 70 and causes deflection of the tip portion 60 of the catheter. The mechanical advantage achieved by this rotation-to-axial translation provides a passive resistance or passive lock of sufficient frictional force so as to prevent the tip deflection angle from changing without further manipulation of the thumbwheel 25 by the user.

In certain prior art deflectable tip type steerable catheters, upon the user's desire to relax or straighten the deflectable portion, the pullwire 70 is advanced in the opposite direction from that which caused deflection of the tip. It has been discovered that in the case where deflection is caused by placing tension on the pullwire, it is not desirable to place the pullwire in compression. While relatively stiff, the pullwire is subject to buckling and subsequent cold fracture when repeatedly and successively place under tension and compression. Accordingly, the proximal part 90 of the two-part slideblock according to the invention has no similar external threads or wings corresponding to the helically disposed wings 82,84 of the distal part of the slideblock. Thus, upon counter rotation of the thumbwheel 25, the distal part 80 travels distally until the indicator ring 45 signifies that the tip is in a fully relaxed position as described hereinabove. At that point, natural resiliency of the distal portion 60 will tend to straighten out the tip and will place the pullwire 70 under some tension. Even though very slight, the amount of tension is sufficient to avoid buckling and fracture of the pullwire 70. In addition, withdrawing the catheter from the anatomical site under investigation will also tend to straighten out the catheter for ease of withdrawal.

The variable radius of curvature feature of the invention is now described in connection with FIGS. 2 and 3. Selectable distance D is determined by the user's positioning of the slide actuator 26 on the control handle 20. In the distal-most position of slide actuator 26, the free end 50 of adjusting wire 42 extends into the softer flexible length of the distal tip portion beyond the junction 51 between that tip portion and relatively stiffer main catheter shaft 40, as shown in the upper portion of FIG. 3.

In an alternative preferred embodiment, the free end 50 is slightly proximal of the junction 51 when the slide actuator 26 in its proximal-most position, in order to create a more stepped transition in stiffness from the main shaft 40 to the soft tip portion 60. The stiffest portion would be the main shaft 40 with the adjusting wire 42 therein; somewhat less stiff would be the main catheter shaft 40 without the adjusting wire 42, and least stiff would be the soft tip portion 60 alone.

Returning to FIGS. 2 and 3, upon proximal sliding action of the slide actuator 26 by the user, the free end 50 is brought back to a position substantially near the junction 51 between the softer and relatively stiffer portions of the catheter, as shown in the lower portion of FIG. 3. Because the tip portion 60 will bend substantially only in areas where it is relatively soft, presence of the adjusting wire 42 serves to define and effective length of flexible soft material of the distal tip portion 60. Bending of the tip generally begins only at the transition point between relatively stiff and relatively softer materials. Since the throw or length of travel of the two-part slideblock is the same in any case, a smaller length of relatively soft material is caused to bend with a sharper radius of curvature when the pullwire 70 (not shown in FIG. 3) is retracted proximally. Thus, distal tip portion can be curved with a small radius to maneuver within a small cavity.

On the other hand, when the adjusting wire 42 is positioned so that its free end 50 is substantially coincident with or proximal to the boundary or junction 51 between the relatively stiffer material of the main catheter shaft 40 and the distal tip portion 60, a substantially long, soft, flexible segment of the distal tip portion 60 is defined. Here, when the pullwire 70 is selectively retracted in the proximal direction, the distal end of the tip portion 60 bends about the junction 51 to create a substantially larger radius of curvature. This allows the electrophysiologist to bend the flexible portion of the distal tip 60 a further distance from the longitudinal axis of the catheter main shaft 40 at the junction 51. In this way, the user may conveniently reach a more distant anatomical site for electrophysiological recording, mapping, ablation, etc.

Thus, as illustrated by FIG. 3, both the radius of curvature and the degree of deflection of the distal portion 60 are easily selectable by the user's manipulation of the thumbwheel 25 in conjunction with the slide actuator 26 of the control handle 20. The more the pullwire is retracted proximally, the larger the deflection angle of the distal tip will be. The further distally the adjusting wire 42 is telescoped passed the junction 51 between the relatively soft tip portion 60 and relatively stiff catheter main shaft 40, the smaller the radius of curvature will be. Thus, the electrophysiologist can vary the deflection of the distal tip 60 to maneuver in both small and large cavities, and may more easily reach both relatively near and more distant sites.

A presently preferred embodiment of the invention, without the radius of curvature adjustment feature, is commercially available from C. R. Bard, Inc., assignee of the presently described inventions, and is identified as a BARD ELECTROPHYSIOLOGY EP•XT™ Steerable Catheter, which is a radiopaque flexible insulated electrode catheter constructed of a polyurethane main shaft and all solid platinum electrodes.

The following are preferred materials for use in making the present invention.

The ring electrodes 62 and tip electrode 64 are pure (99%) platinum. The electrode wires are 0.005" diameter copper wire, with approximately 0.001" thick insulation thereon. The soft tip portion 60 is made of KJ-5 polyurethane, supplied by USCI Division of C. R. Bard, Inc. The main catheter shaft 40 is also made of KJ-5 polyurethane, reinforced with a wire braid. The main shaft 40 may also be stiffened with tetrafluoroethylene (TEFLON) tubing, 0.059" O.D.×0.038" I.D., or acrylic/polyurethane (ISOPLAST) tubing, 0.059" O.D.×0.026" I.D. The pullwire is 304 Stainless Steel, 0.008" diameter. The control handle 20 is molded from modified polyphenylene oxide (NORYL), as are most of the handle subcomponents. The thumbwheel is molded acetal (DELRIN). The proximal part 90 of the slideblock is 304 Stainless Steel, as are the spacers 57. The guide tube 38 is acrylic/polyurethane, 0.049" O.D.×0.026" I.D. The O-rings 59, 77 are silicone 0.50" I.D.×0.070" diameter cross section. The connector 30 is molded polybutylene terepthalate and includes gold-plated copper terminals.

While there have been shown and described fundamental novel features as applied to a preferred embodiment thereof, it will be understood that omissions and substitutions and changes in the form of details of the disclosed device, and in its manner of assembly and operation, may be made by those skilled in the art without departing from the spirit of the invention. It is the intention, therefore, to be limited only as indicated by the scope of the claims appended hereto.

Illustratively, although the steerable catheter of the present invention is expressly disclosed for use in sensing electrical signals in body tissues and applying electric signals to such tissues, a catheter so designed may be readily and suitably modified for use in the transfer of fluids (liquid or gas) into or out of a patient. In such an alternate embodiment, the electrical contacts, the conductive wires and the electrical connector may be eliminated. Instead, appropriate through holes or lumens may be provided in the catheter's tip portion and appropriate fluid transfer apparatus connected to the proximal end of the lumens so as to provide irrigation or aspiration capabilities. Similarly, optical fibers may be provided instead of, or in addition to, electrical conductors. In such an embodiment one or more optical fibers may be connected to a light source, such as a laser, while one or more other optical fibers are connected to a video camera and/or similar viewing or recording devices. Alternatively, a longitudinally movable rigid cable equipped with various manipulatable devices may be extendable distally through a bore or lumen in the catheter's tip portion for removal of patient tissue for biopsy, or for use in other surgical procedures such as removal or destruction of atherosclerotic plaque or other diseased body tissue. Any one or more of these alternative embodiments may be combined one with another for a particular use contemplated or intended for a tip deflectable, steerable catheter.

Finally, as will be readily apparent to those skilled in the art the dimensions stated relate to one particular catheter size and are disclosed solely by way of example and should not, therefore, be understood as an intended limitation on the scope of the invention.

What is claimed is:

1. A deflectable tip steerable catheter comprising:

a control handle;

a catheter shaft having a proximal end attached to the control handle and having a distal end;

a deflectable tip portion having a proximal end attached to the catheter shaft distal end, the tip portion also having a distal end, wherein the tip portion has an adjustable radius of curvature;

a pullwire attached off-axis to the deflectable tip portion near its distal end, the pullwire extending proximally through the tip portion, through the catheter shaft and into the control handle for deflecting the tip portion between an undeflected position and a fully deflected position; and means for varying the radius of curvature of the tip portion when in the fully deflected position from a relatively small fully deflected radius of curvature to a relatively large fully deflected radius of curvature.

2. The deflectable tip steerable catheter of claim 1 wherein said control handle includes an actuator, and wherein said means for varying the radius of curvature of the tip portion comprises a stiff adjusting wire connected to said control handle, said adjusting wire being slidable in response to movement of the actuator within said control handle, said adjusting wire extending distally through said catheter shaft and into said deflectable tip portion, said adjusting wire being proximally and distally movable within said deflectable tip portion.

3. The deflectable tip steerable catheter of claim 2 wherein said actuator comprises a slide actuator attached to said proximal end of said adjusting wire for slidably moving said adjusting wire distally and proximally within said deflectable tip portion.

4. The deflectable tip steerable catheter of claim 1 wherein the means for varying the radius of curvature of the tip portion varies the radius of curvature of the tip portion at any given position during deflection, by the pullwire, between the undeflected position and the fully deflected position.

* * * * *